United States Patent
Scholz

(10) Patent No.: US 7,583,994 B2
(45) Date of Patent: Sep. 1, 2009

(54) APPARATUS FOR LOCALIZING A FOCAL LESION IN A BIOLOGICAL TISSUE SECTION

(75) Inventor: Bernhard Scholz, Heroldsbach (DE)

(73) Assignee: Siemens Aktiengesellschaft, Munich (DE)

( * ) Notice: Subject to any disclaimer, the term of this patent is extended or adjusted under 35 U.S.C. 154(b) by 362 days.

(21) Appl. No.: 10/792,570

(22) Filed: Mar. 3, 2004

(65) Prior Publication Data

US 2004/0230112 A1 Nov. 18, 2004

(30) Foreign Application Priority Data

Mar. 3, 2004 (DE) ................... 103 09 245

(51) Int. Cl.
*A61B 5/06* (2006.01)
*A61B 5/04* (2006.01)
(52) U.S. Cl. ............... 600/547; 600/544; 600/546
(58) Field of Classification Search ........... 600/547, 600/546, 554
See application file for complete search history.

(56) References Cited

U.S. PATENT DOCUMENTS 5,623,939 A * 4/1997 Garfield ............... 600/546
5,984,870 A * 11/1999 Giger et al. ............ 600/443
6,201,990 B1 * 3/2001 Wexler et al. .......... 600/547
2003/0004432 A1 1/2003 Assenheimer

FOREIGN PATENT DOCUMENTS

DE 101 58 151 6/2003
WO WO 99/48422 9/1999

OTHER PUBLICATIONS

"Towards Virtual Electric Brest Biopsy: Space-Frequency MUSIC for Trans-Admittance Data," Scholz, IEEE Trans. On Med. Imaging, vol. 21, No. 6, Jun. 2002, pp. 588-595.

* cited by examiner

*Primary Examiner*—Max Hindenburg
*Assistant Examiner*—Jeffrey G Hoekstra
(74) *Attorney, Agent, or Firm*—Schiff Hardin LLP

(57) ABSTRACT

An apparatus for localizing a focal lesion in a biological tissue section applies electrical excitation signals to the tissue section and measures electrical response signals at a number of measurement locations on a surface of the tissue section that arise there due to the excitation signals. A computer reconstructs a distribution of electrical dipole moments from the response signals, this distribution of dipole moments overall best reproducing the response signals, and supplies the 3D spatial position of the distribution as an output.

5 Claims, 4 Drawing Sheets

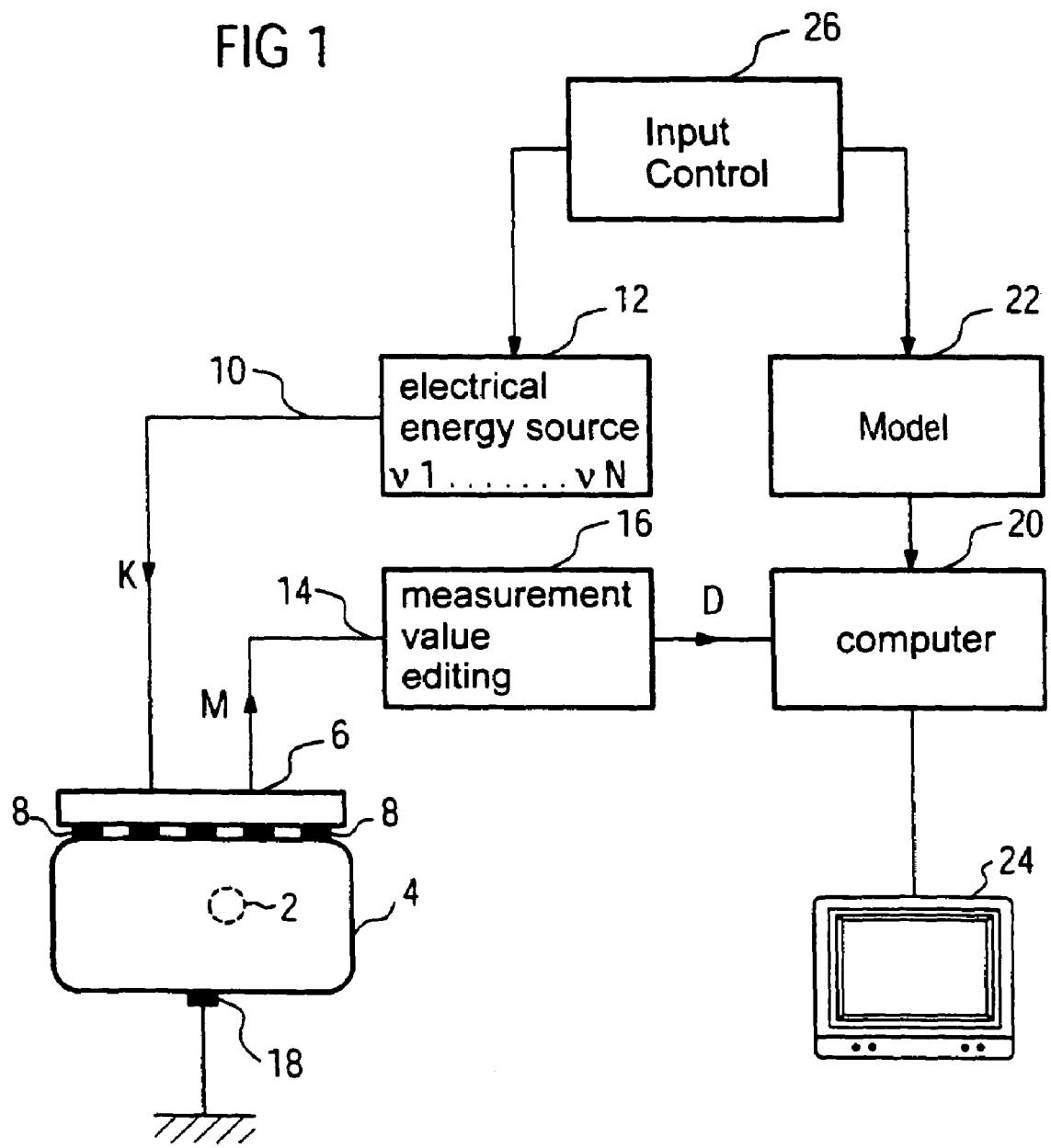

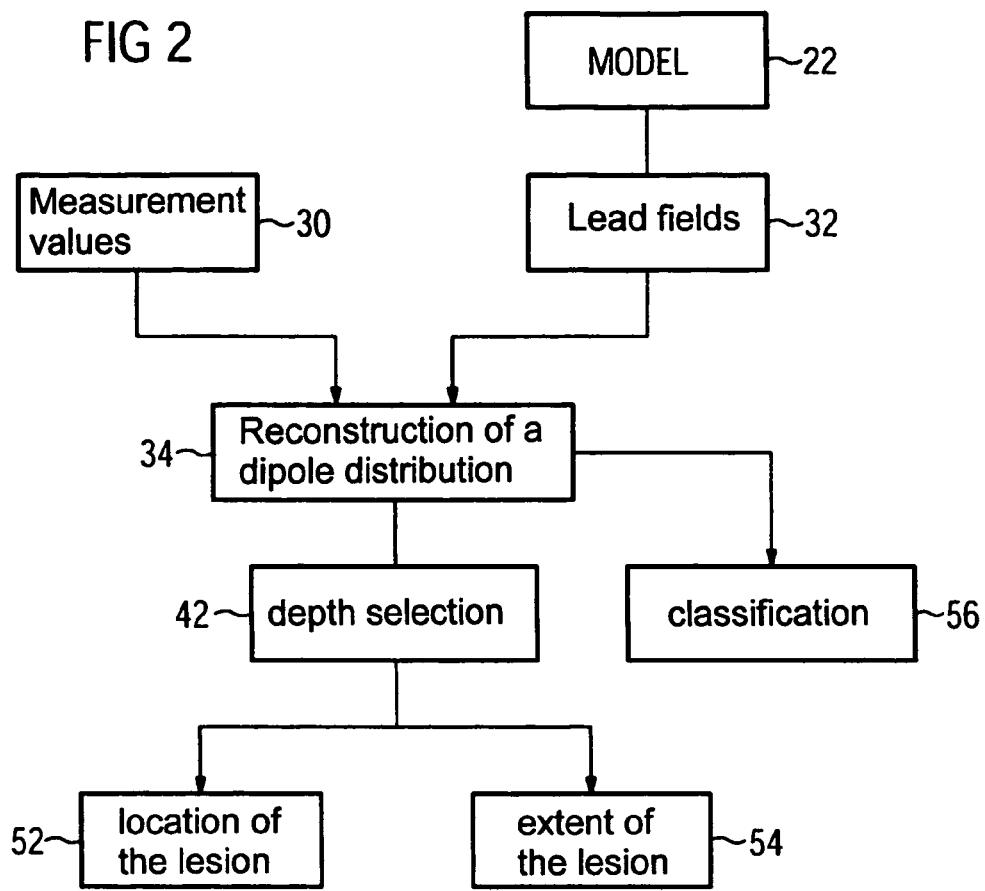
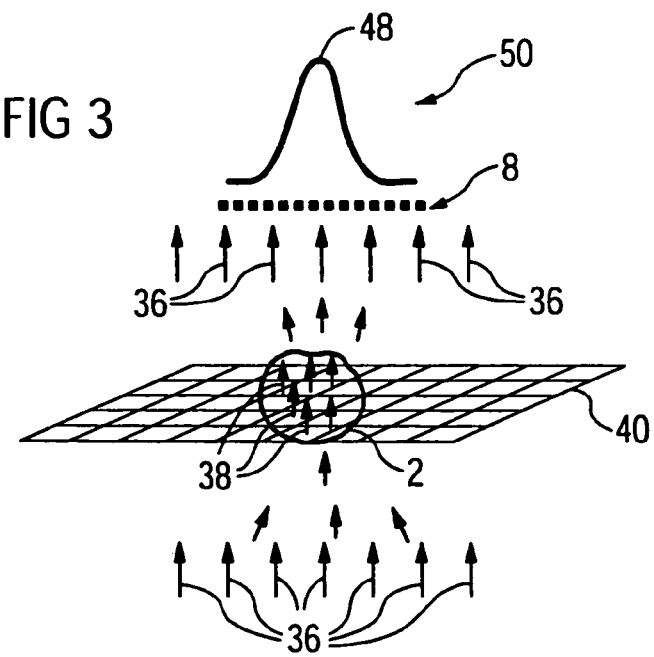

APPARATUS FOR LOCALIZING A FOCAL LESION IN A BIOLOGICAL TISSUE SECTION

BACKGROUND OF THE INVENTION

1. Field of the Invention

The invention concerns an apparatus for localizing a focal lesion in a biological tissue section, the lesion exhibiting an electrical property different from the tissue section, and the electrical property in the tissue section being essentially constant, of the type having means to apply electrical excitation signals to the tissue section and with means to measure electrical response signals at a number of measurement locations on a surface of the tissue section that arise due to the excitation signals.

2. Description of the Prior Art

In imaging by means of electrical impedance, alternating voltages are applied to a tissue section to be examined at one or more locations, and/or electrical alternating currents are applied. Using measurement electrodes that are electrically contacted to the tissue section to be examined at a number of locations, currents (amplitude and phase) are measured that arise due to the applied voltages, and/or voltages (amplitude and phase) are measured that arise due to the applied currents and due to the electrical conductivity distribution of the subject. This method is at present used particularly for examination of lesions in a female breast.

An apparatus of the initially cited type is known from PCT Application WO 99/48422. The apparatus has a current or voltage source that is connected with electrodes. The current source (or the voltage source) generates a series of currents (or voltages) of different frequency that are supplied via the electrodes as excitation signals to a body section to be examined. Based on the excitation signals, lesions present within the body section generate response signals that are supplied to a measurement value-editing (or conditioning) unit via the aforementioned electrodes. The response signals are determined by the electrical properties (specified, for example, by a mathematically complex conductivity) of the subject having the lesion. The measurement value-editing unit is connected with a computer to which the edited measurement values and a model of the tissue section are supplied. From the edited measurement data and the model, the lesion is determined from the signal activity by means of a reconstruction method running on the computer, and its spatial position is determined.

For example, 64 or 256 time-dependent current values on the surface of a female breast can presently be measured with the commercially available device TS2000 from the company TransScan by means of 8×8 or 16×16 regularly arranged electrodes on a measurement surface of approximately 7.9× 7.9 cm$^2$. The current values arise as a result of an alternating voltage between measurement electrodes and a reference electrode held by the examination subject in the contralateral hand. The measurement data, (magnitude and phase of the current) are individually calculated as conductance and capacitance and are represented corresponding to the two-dimensional electrode arrangement.

If focal lesions that, for example, exhibit a higher electrical conductivity than the surrounding tissue, are located in the tissue section below the measurement electrodes, then (for example in the case of current measurements) higher current values are measured in the electrodes directly above them. Such a lesion is visible as a peak in the two-dimensional measurement data representation. The peak amplitude and the peak width depend on the size and depth of the lesion and on the conductivity difference between the lesion and the surrounding tissue.

The conductivities, in particular of breast tissue, are known both from the clinical practice and from tissue samples measured in vitro. The presence of a peak, however, still allows no clear conclusion about the malignity of the lesion.

SUMMARY OF THE INVENTION

An object of the present invention is to provide an apparatus for localizing a lesion with which an at least two-dimensional spatial reconstruction of lesions of arbitrary shape and size can be determined from admittance data, and therewith the spatial position of the lesion.

The object is achieved in an apparatus wherein admittance signals are obtained as described above and supplied to a computer that reconstructs a distribution of electrical dipole moments from the response signals, which distribution of dipole moments overall best reproduces the response signals, and wherein the computer also determines, and supplies as an output, the spatial position of the distribution. In contrast to the previously cited device (in which a signal activity is determined at a single location for each lesion), in the inventive apparatus an at least planar (2D) dipole distribution is determined which is used as a measure for the spatial extent of the lesion.

In an embodiment of the invention the computer classifies the lesion dependent on the frequency response of the dipole distributions. Conclusions can be made about the tissue type from the frequency response of the dipole moments in the area of the lesion. The admittance measurements are then effected in a frequency range in which the cited conductivity differences and consequently also polarization differences, between malignant and benign tissue, are characteristic. The apparatus thus facilitates a function diagnostic using frequency-dependent admittance data. This ensues, for example, by a classification in which the dipole distribution is associated with a benign or malignant lesion.

DESCRIPTION OF THE DRAWINGS

FIG. 1 is a block diagram of the basic components of a device to localize a focal lesion in a tissue section in accordance with the invention.

FIG. 2 shows the basic method steps to localize and classify a focal lesion in accordance with the invention.

FIG. 3 schematically illustrates a polarized lesion with a distribution of dipoles, as well as the curve of the corresponding measurement values at the measurement electrodes obtained in accordance with the invention.

DESCRIPTION OF THE PREFERRED EMBODIMENTS

Figure 4A:
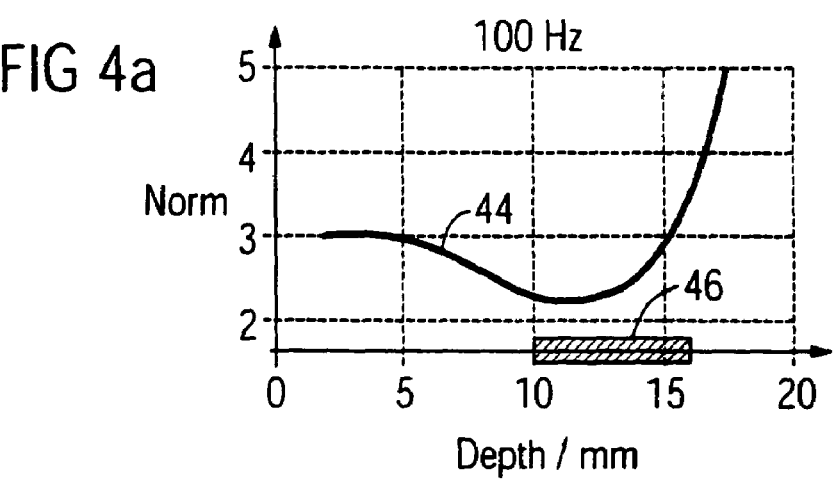
FIGS. 4a through 4f respectively show curves of the norm of the dipole reconstruction, dependent on depth, for different frequencies, obtained in accordance with the invention.

The overview representation in FIG. 1 shows the basic design of a measurement and evaluation arrangement with which signal activities of a limited spatial area 2 can be localized and identified in a biological tissue section 4. It is thereby assumed that the spatial area 2 possesses an electrical conductivity different from the rest of the tissue section 4, and the rest of the tissue section 4 exhibits an essentially spatially constant electrical conductivity. These assumptions are fulfilled sufficiently well when the biological tissue section 4 is a female breast and the limited spatial area 2 is a tumor.

The measurement arrangement includes an applicator 6 with a number of spatially distributed, arranged electrodes 8 that are contacted with the surface of the tissue section 4. In FIG. 1, for clarity only five electrodes 8 are shown, however, for a sufficiently precise localization, for example M=256 electrodes 8 should be arranged on a surface of 9×9 cm$^2$.

The electrodes 8 are connected to an electrical energy source (current source or voltage source) 12 via electrical connection lines 10, as well as to a measurement value-editing unit 16 via electrical connection lines 14. A counter-electrode 18 is arranged on the side of the tissue section 4 opposite the applicator 6, this counter-electrode also being connected to the energy source 12 and to the measurement value preparation 16. It is also possible to fashion a part of the applicator 6 as a counter-electrode.

With the aid of the electrical energy source 12, alternating currents (in the case of potential measurements) or alternating voltages (in the case of current measurements) are supplied to the biological tissue section 4 via a number K of the electrodes 8, whereby 1≦K≦M, in order to generate a spatial current distribution. Limited spatial areas 2 that have a different electrical conductivity than the surrounding tissue 4 are electrically polarized by the externally fed currents or applied voltages in such a manner that the now-polarized spatial area 1 can now be approximately viewed as a focal bioelectrical signal source. The signal strength of this source depends on the size of the spatial area 2 and on the frequency-dependent complex conductivity of the spatial area 2.

The localization and identification of the spatially limited area 2 follow from the locating and the determination of the strength of such bioelectric signal sources, by the potentials generated by the fed currents on the surface of the tissue section 4 at the M electrode locations being measured and evaluated. Since the frequency dependence of the electrical conductivity in the limited spatial areas 2 represents an important measure for characterization (classification) or identification of the corresponding tissue, currents or voltages from the energy source 12 can be generated at N different frequencies (that, for example, lie in the range from 100 Hz to 500 Hz) and supplied to the tissue section 4.

The measurement value-editing unit 16 includes, for example, measurement amplifiers, filters and analog-digital converters. The measurement value-editing unit 16 is connected to one or more data inputs of an electronic computer 20. In addition to the measurement values, a model 22 of the tissue section 4 is made available to the computer 20, with which the bioelectric signal sources mentioned above are localized and identified, as specified further below. The result, for example in the form of a graphic representation of the anatomy of the tissue section wherein the location of the signal sources, and therewith the spatial area 2, is marked, ensues via a monitor 24. Additionally, a quantity characterizing the signal activity is shown that is dependent on the current or voltage frequencies. Since the model 22, among other things, is determined by the generated current pattern in the tissue section 4 and the in-feed location, a superordinate input and control 26 is provided with which the number and the location of the electrodes 8, the value of the current or voltage frequency, and the model are predetermined.

The substantial signal processing and signal evaluation steps that are implemented by the measurement and evaluation arrangement according to FIG. 1 are explained in the following.

The admittance values 30 measured given a frequency $f_k$ (k=1 . . . , K) at M locations are combined into an M-dimensional data vector $\underline{Y}_k$. It is $$\underline{Y}_k = (Y_k(\vec{r}_1), \ldots, Y_k(\vec{r}_M))^T, \quad (1)$$

wherein $\underline{Y}_k(\vec{r}_m) = \underline{G}_k(\vec{r}_m) + i2\pi C_k(\vec{r}_m)$. G and C are the conductance and capacitance, which are associated with the respective measurement location given the frequency $f_k$.

Individual vectorial dipole leads fields 32 belong to the model 22, represented as $\vec{L}_n(\vec{r}_m, \vec{n}_m) \equiv \vec{L}_n(\vec{r}_m, \vec{n}_m, \vec{r}_n)$, (n=1, . . . , N), that define measurement value distributions of a dipole at location $\vec{r}_n$ whose vectorial components respectively possess the strength one. The lead fields depend on the electrical model of the tissue section 2 (here a volume conductor model), on the type of the measurement (potential and/or current measurement, here current measurement), the measurement location $\vec{r}_m$ and the normal vector $\vec{n}_m$ with regard to the measurement electrode, and on the dipole location $\vec{r}_n$.

The measurement values 30 and the leads fields 32 are input data for a dipole distribution reconstruction unit 34 that operates in the computer 20 with a suitable control program.

The physical bases of the reconstruction are illustratively shown in FIG. 3. In the exemplary case of current measurements, the admittance data $\underline{Y}_k$ are caused by an externally-excited electrical background field 36 and an induced dipole moment distribution 38 as a result of the tissue polarization, in particular the polarization of the lesion.

Initially, the admittance value determined at the location $\vec{r}_m$ is given by the measured current density $\vec{j}$, the normal vector $\vec{n}_m$ on the electrode surface at the measurement location, the value of the electrode surface $A_{Electr}$, and the amplitude $U_0$ of the applied alternative voltage:

$$Y_k(\vec{r}_m) = \vec{n}_m \cdot \vec{j}(\vec{r}_m, f_k) \frac{A_{Electr}}{U_0} \quad (2)$$

The index k and the quantity $f_k$ designate the k$^{th}$ measurement frequency. Assuming an induced dipole moment distribution 38, the current density can be expressed via the electrical background field $\vec{E}_{bgrd}$, the conductivity $K_{sur}$ at the measurement surface, and via the vectorial dipole moments $\vec{d}(\vec{r}_n, f_k)$ linked with the N vectorial guide fields at the voxel/pixel locations $\vec{r}_n$, (n=1, . . . , N) of the gridded tissue section 2:

$$\vec{n}_m \cdot \vec{j}(\vec{r}_m, f_k) = K_{sur}(f_k) \vec{n}_m \cdot \vec{E}_{bgrd}(\vec{r}_m, f_k) + \Sigma_{n=1}^N \vec{L}(\vec{r}_m, \vec{n}_m, \vec{r}_n) \cdot \vec{d}(\vec{r}_n, f_k) \quad (3)$$

Using vector and matrix notation, equation (3) can be written more compactly. The vector of the normal components (introduced above) of the current densities—with f as frequency—is $$\underline{j}(f) = (j_1(f), \ldots, j_M(f))^T \text{ with } j_m(f) = \vec{n}_m \cdot \vec{j}(\vec{r}_m, f) \quad (4)$$

The vector of the normal components of the electrical background field is defined in a corresponding manner.

$$\underline{E}_{bgrd}(f) = (E_{bgrd,1}(f), \ldots, E_{bgrd,M}(f))^T \text{ with } E_{bgrd,m}(f) = \vec{n}_m \cdot \vec{E}_{bgrd}(\vec{r}_m, f) \quad (5)$$

Consequently, the current density Eq to be associated with the background field is $$j_{bgrd}(f) = K_{sur}(f) \underline{E}_{bgrd}(F) \tag{6}$$

The entirety of the leads fields is combined into an M×3N matrix L.

$$L = \begin{bmatrix} L_x(\vec{r}_1, \vec{r}_1) & L_y(\vec{r}_1, \vec{r}_1) & L_z(\vec{r}_1, \vec{r}_1) & \cdots & L_z(\vec{r}_1, \vec{r}_N) \\ \vdots & \vdots & \vdots & \ddots & \vdots \\ L_x(\vec{r}_M, \vec{r}_1) & L_y(\vec{r}_M, \vec{r}_1) & L_z(\vec{r}_M, \vec{r}_1) & & L_z(\vec{r}_M, \vec{r}_N) \end{bmatrix} \tag{7}$$

The dipole moments at the N locations form a 3N-dimensional column vector.

$$d(f) = (d_x(\vec{r}_1, f), d_y(\vec{r}_1, f), d_z(\vec{r}_1, f), \ldots, d_x(\vec{r}_M, f), d_y(\vec{r}_M, f), d_z(\vec{r}_M, f))^T \tag{8}$$

The equation (3) is, in matrix notation, $$\underline{j}(f_k) = \underline{j}_{bgrd}(f_k) + L \cdot d(f_k) \tag{9}$$

The determination equation of the distributed, induced dipoles results from the admittance data according to equation (2) by multiplication of the equation (9) with $A_{Electr}/U_0$.

$$\underline{Y}(f_k) = \underline{Y}_{bgrd}(f_k) + L \cdot d(f_k) \frac{A_{Electr}}{U_0} \equiv \underline{Y}_{bgrd}(f_k) + L \cdot \tilde{d}(f_k) \tag{10}$$

The solution to equation (10) represents an algebraic reconstruction problem. Methods to solve such inverse problems, for example in image processing, are discussed in the literature.

The solution ensues, for example, in planes of different depth parallel to the measurement plane, meaning distance from the measurement surface. In FIG. 3, a single plane 40 is either known or is determined via an algorithmic depth selection method explained further below.

The treatment of the unknown inhomogeneity term $\underline{Y}_{bgrd}$ in equation (10) can ensue in two ways:
1. the measurement value contribution from $\underline{Y}_{bgrd}$ is negligible.
2. the contribution of $\underline{Y}_{bgrd}$ is eliminated via subtraction.

One possible subtraction technique are to estimate this background contribution from the edge data when it can be assumed that the lesion signal at the ends has fallen off and to subsequently subtract the estimated background values. Another possible technique is to make a measurement of a data set in direct proximity to the lesion, but without the lesion signal, under the assumption that the background contribution thus is being measured, and to subsequently subtract the measured background value.

The result of these measures is a reduction of the equation (10) to $$\underline{Y}_{sub}(f_k) = L \cdot \tilde{d}(f_k) \tag{11}$$

A solution to equation (11) is $$\tilde{d}(f_k) = L^+ \underline{Y}_{sub}(f_k), \tag{12}$$

wherein $L^+$ is the generalized inverse matrix of L. In the event of poor numerical condition of the lead field matrix, the generalized inverse results in the over-determined, or in the under-defined case as follows $$L^+ = (L^T L + \gamma 1)^{-1} L^T \text{ in the event that } M > 3N \text{ (over-defined)} \tag{13}$$

$$L^+ = L^T (LL^T + \gamma 1)^{-1} \text{ in the event that } M < 3N \text{ (under-defined)} \tag{14}$$

The parameter γ is called the regularization parameter.

Equation (11) is solved with normalized guide fields in an advantageous depth-first search method. The norm $\|d\|$ of the determined dipole distributions for each plane 40 is plotted dependent on the depth. Since the depth determination is independent of the background field, this contribution can remain unconsidered at this point.

Based on the solution properties (solutions with minimum norm), it can thereby be expected that the specified curve $\|d\|$ over the depth (for example, z-coordinate) possesses minima in the depth direction where a lesion is located.

Figure 4B:
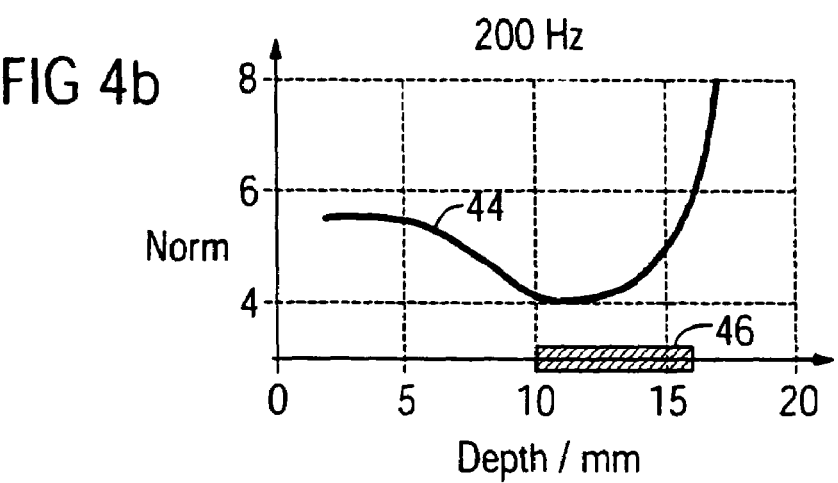
Figure 4C:
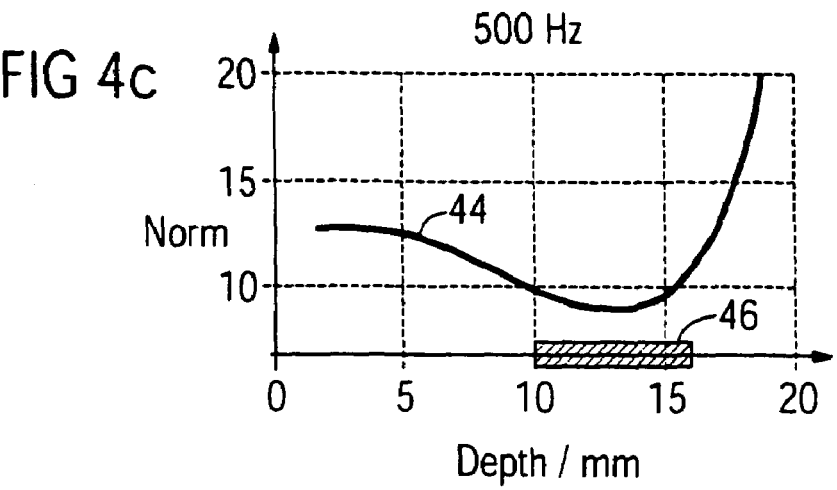
Figure 4D:
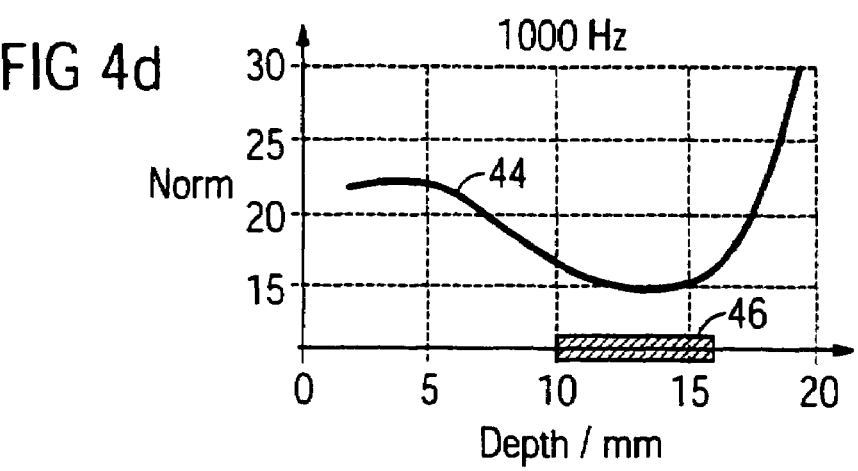
Figure 4E:
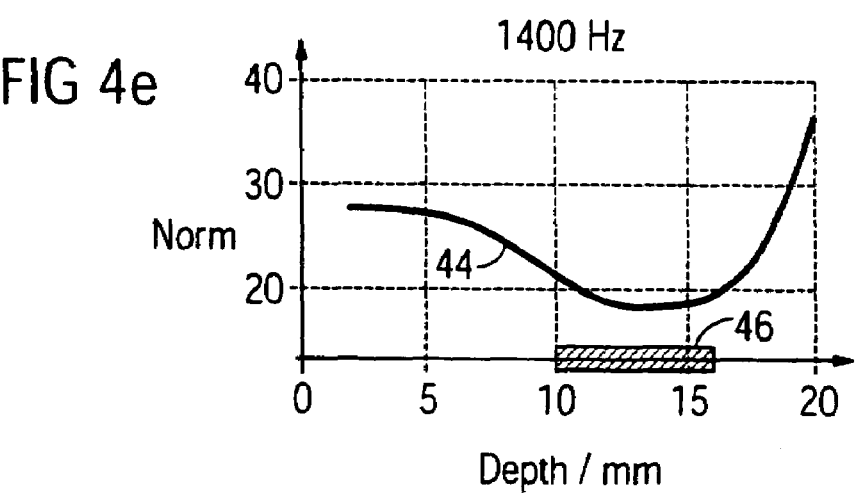
Figure 4F:
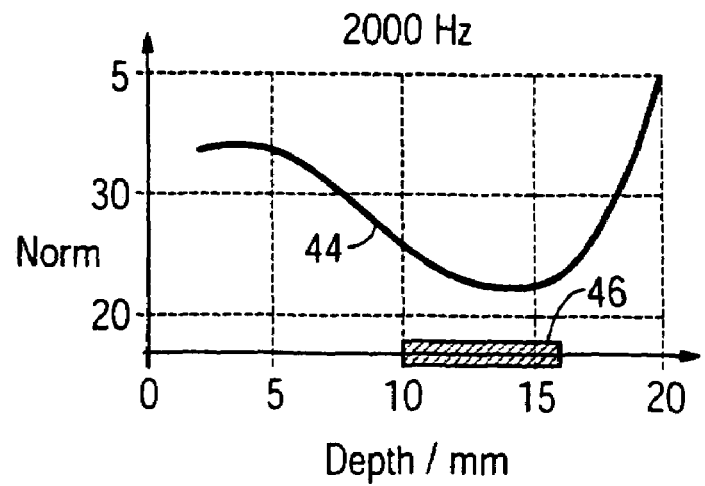

FIGS. 4a through 4f show the norm $\|d\|$ of the dipole distributions respectively for each measurement frequency over the depth of the curve 44. In FIGS. 4a through 4f, a region 46 is additionally emphasized that specifies the depth expansion of the lesion 2 as it has been determined from an ultrasound measurement.

Due to its increased polarizability, a lesion produces—as a result of high electrical conductivity in comparison to the surroundings—increased dipole moments in the lesion region. Thus, a peak 48 in the calculated two-dimensional dipole moment distribution 50 can be considered as the location of the lesion. The depth plane of the lesion 2 results from the analysis described above of the norm of the dipole distributions. The location of the lesion 2 in space is thereby determined as a localization result 52. The extent of the lesion is determined from the width of the peak region in the dipole moment distribution 38. The depth extent results from the analysis of the norm. The extent of the lesion in all three spatial directions thus is determined, and can be output as a further localization result 54.

The frequency dependency of the dipole moments is determined by the electrical conductivity of the lesion. Since the electrical conductivities of malignant and benign tissue types exhibit different frequency responses, a different frequency response is also to be expected for the dipole moments associated with them. The diagnostic information content of the dipole frequency response is based on this. This response is evaluated in a classification 56 of the lesion 2.

Although modifications and changes may be suggested by those skilled in the art, it is the intention of the inventor to embody within the patent warranted hereon all changes and modifications as reasonably and properly come within the scope of his contribution to the art.

I claim as my invention:

1. An apparatus for localizing a focal lesion in a biological tissue section, said lesion exhibiting an electrical property that is different from said electrical property of the tissue section, and wherein said electrical property in the tissue section is substantially constant, said apparatus comprising:

a measurement arrangement configured to interact with the tissue section, to apply electrical excitation signals to said tissue section that polarize bioelectric signal sources in said tissue section to produce a distribution of electrical dipole moments in said tissue section, and to measure electrical response signals that occur in response to said excitation signals, and that collectively represent said distribution of electrical dipole moments, at a plurality of measurement locations on a surface of the tissue section; and a computer supplied with signals corresponding to said electrical response signals, said computer being programmed to reconstruct said distribution of electrical dipole moments from the signals supplied to the computer as a reconstructed distribution that overall best reproduces said signals supplied to the computer, and to determine, from said reconstructed distribution, a three-dimensional spatial location of said lesion and to determine, from said signals corresponding to said electrical response signals, an indicator as to whether said lesion is pathological, and to make said three-dimensional location and said indicator available as a humanly perceptible output.

2. An apparatus as claimed in claim 1 wherein said computer has a memory containing a gridded model of the biological tissue section and is programmed to generate leads fields that describe said signals supplied to the computer with respect to electrical dipole moments, in said distribution of electrical dipole moments at respective locations in said model.

3. An apparatus as claimed in claim 2 wherein said computer is programmed to determine a depth location of said lesion in said tissue as a part of said 3D spatial location, by determining, from said distribution of electrical dipole moments, respective distributions of electrical dipole moments in a plurality of layers in said model, and by identifying a layer among said plurality of layers having a distribution of electrical dipole moments therein with a minimum energy as representing the depth location of the lesion in the tissue section.

4. An apparatus as claimed in claim 1 wherein said measurement arrangement applies a series of said electrical excitation signals to said tissue section at respectively different frequencies, and wherein said computer is programmed to reconstruct said distribution of electrical dipole moments for each of said frequencies, thereby producing a plurality of distributions of electrical dipole moments for the respective frequencies.

5. An apparatus as claimed in claim 4 wherein said computer is programmed to classify said lesion, with respect to pathology, dependent on a frequency response of the respective of electrical dipole moments, and to include a classification of said lesion as said indicator in said humanly perceptible output.

* * * * *